(12) United States Patent
Saito et al.

(10) Patent No.: US 8,377,664 B2
(45) Date of Patent: *Feb. 19, 2013

(54) METHOD FOR PRODUCING A USEFUL SUBSTANCE BY USE OF AN IMMOBILIZED ENZYME

(75) Inventors: Jun Saito, Kamisu (JP); Yoshitaka Senda, Kamisu (JP); Toshiteru Komatsu, Kamisu (JP)

(73) Assignee: Kao Corporation, Tokyo (JP)

( * ) Notice: Subject to any disclaimer, the term of this patent is extended or adjusted under 35 U.S.C. 154(b) by 965 days.

This patent is subject to a terminal disclaimer.

(21) Appl. No.: 12/067,664

(22) PCT Filed: Oct. 4, 2006

(86) PCT No.: PCT/JP2006/320249
§ 371 (c)(1),
(2), (4) Date: Mar. 21, 2008

(87) PCT Pub. No.: WO2007/043552
PCT Pub. Date: Apr. 19, 2007

(65) Prior Publication Data
US 2009/0298142 A1 Dec. 3, 2009

(30) Foreign Application Priority Data

Oct. 5, 2005 (JP) ................ 2005-292203

(51) Int. Cl.
*C12P 7/64* (2006.01)
*C12N 11/00* (2006.01)
*C12N 11/14* (2006.01)

(52) U.S. Cl. ............. 435/134; 435/174; 435/175

(58) Field of Classification Search ........... 435/109, 435/44, 137, 41, 176, 134, 147, 136; 422/405, 422/503, 527, 535, 549, 562, 569
See application file for complete search history.

(56) References Cited

U.S. PATENT DOCUMENTS

| | | | |
|---|---|---|---|
| 4,292,409 A | 9/1981 | Cremonesi | |
| 4,629,742 A * | 12/1986 | Brady et al. | 521/55 |
| 4,678,580 A | 7/1987 | Brady et al. | |
| 4,833,083 A * | 5/1989 | Saxena | 435/403 |
| 5,010,004 A * | 4/1991 | Kosugi et al. | 435/134 |
| 5,292,649 A * | 3/1994 | Kosugi et al. | 435/136 |
| 2003/0013165 A1 * | 1/2003 | Komatsu et al. | 435/134 |

FOREIGN PATENT DOCUMENTS

| | | |
|---|---|---|
| CN | 85 1 00111 A | 7/1986 |
| CN | 85100111 A * | 7/1986 |
| DE | 41 25 186 | 2/1993 |
| DE | 4125186 A1 * | 2/1993 |
| EP | 1 004 662 | 5/2000 |
| EP | 1 657 303 | 5/2006 |
| JP | 61-085195 | 4/1986 |
| JP | 63 59896 | 3/1988 |
| JP | 1-98494 | 4/1989 |
| JP | 4 335881 | 11/1992 |
| JP | 2000-160188 | 6/2000 |
| JP | 2001-314735 | 11/2001 |
| JP | 2005 65632 | 3/2005 |
| WO | 92 18636 | 10/1992 |

OTHER PUBLICATIONS

U.S. Appl. No. 12/517,574, filed Jun. 4, 2009, Senda, et al.
U.S. Appl. No. 12/518,285, filed Jun. 9, 2009, Saito, et al.
Kimura et al: "Application of Immobilized Lipase to Hydrolysis of Triacylglyceride", European, Journal of Applied Mircobiology and Biotechnology, vol. 17, pp. 107-112 XP001022610, 1983.
Kosugi Y et al: "Continuous Lipolysis Reactor With a Loop Connecting an Immobilized Lipase Column and an Oil-Water Separator", Journal of the American Oil Chemists, vol. 72, No. 11, pp. 1329-1332, XP001022622, 1995.
Office Action issued Jul. 12, 2011 in Japanese Patent Application No. 2006-259909 (with English translation).

\* cited by examiner

*Primary Examiner* — Chris R Tate
*Assistant Examiner* — Douglas F White
(74) *Attorney, Agent, or Firm* — Oblon, Spivak, McClelland, Maier & Neustadt, L.L.P.

(57) ABSTRACT

The present invention provides a method for producing a useful substance by supplying, to a fixed-bed reactor packed with an immobilized enzyme, a liquid mixture containing two liquid phases, in which the two liquid phases are allowed to flow in an identical, parallel direction, which method employs a fixed-bed reactor equipped with an insertion unit or tubes, so as to form a plurality of lumens in the fixed-bed reactor, each lumen having a cross section of a circular shape with a diameter of 100 mm or less or having a polygonal shape with a diagonal line of 100 mm or less, wherein the lumens are packed with an immobilized enzyme and the liquid mixture is supplied. In a reaction performed by passing a reaction mixture exhibiting two liquid phases through a fixed-bed reactor equipped with an immobilized enzyme, overall flow of the reaction liquid is made uniform.

21 Claims, 2 Drawing Sheets

METHOD FOR PRODUCING A USEFUL SUBSTANCE BY USE OF AN IMMOBILIZED ENZYME

FIELD OF THE INVENTION

The present invention relates to a method for producing a useful substance through a reaction carried out in a fixed-bed columnar reactor (hereinafter simply referred to as a fixed-bed reactor) packed with an immobilized enzyme.

BACKGROUND OF THE INVENTION

An immobilized enzyme has conventionally been used in a fixed bed reactor for carrying out, by passing a liquid therethrough, a variety of reactions in relation to the production of L-aspartic acid, production of oils and fats through transesterification, hydrolysis of lactose, hydrolysis of oils and fats, or similar reactions.

These reactions relatively release low heat. Therefore, the reactions are typically carried out in a drum-type reactor, which is the simplest reactor.

As in the case of the hydrolysis of oils and fats, when liquids of two or more species are simultaneously passed through a reactor to which an enzyme has been immobilized, in order to improve reaction efficiency, the liquids are preferably mixed to a uniform state prior to the application thereof to the reactor. In this case, since an oil-phase substrate and a water-phase substrate, which are employed in hydrolysis, are essentially immiscible even after undergoing a mixing operation, in order to attain a uniform phase, they are usually prepared into an emulsion. Meanwhile, since emulsion particles are difficult to reach enzyme molecules that are adsorbed onto the pore walls of a carrier, according to some techniques, the liquid passage rate is controlled to fall within a range such that the reaction mixture will not be emulsified (see Patent Document 1).

In order to pass an oil-phase substrate and a water-phase substrate over the surfaces of a fixed bed, there have been recognized two methods; i.e., a counter flow method (see Patent Documents 1 and 2) and a parallel flow method (see Patent Document 3). Because the former method requires a special scheme and operation method, the parallel flow method is usually employed.

[Patent Document 1] JP-A-S61-85195
[Patent Document 2] JP-A-H01-98494
[Patent Document 3] JP-A-2000-160188

The present invention provides a method for producing a useful substance by supplying, to a fixed-bed reactor packed with an immobilized enzyme, a liquid mixture containing two liquid phases, in which the two liquid phases are allowed to flow in an identical, parallel direction, which method employs a fixed-bed reactor equipped with an insertion unit or tubes, so as to form a plurality of lumens in the fixed-bed reactor, each lumen having a cross section of a circular shape with a diameter of 100 mm or less or having a polygonal shape with a diagonal line of 100 mm or less, wherein the lumens are packed with an immobilized enzyme and the liquid mixture is supplied therethrough.

DETAILED DESCRIPTION OF THE INVENTION

Figure 1:
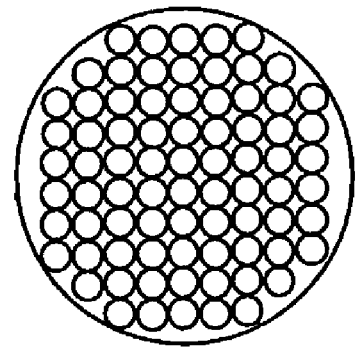
FIG. 1 shows a cross section of an enzyme column equipped with an insertion unit composed of hollow columnar structures.

In a method in which a reaction is carried out by causing a liquid mixture exhibiting two liquid phases to pass through a fixed-bed reactor packed with an immobilized enzyme, when the liquid mixture is applied without undergoing a precedent emulsification procedure, flow of the reaction mixture in the reactor becomes less uniform as the diameter of the reactor becomes larger, leaving portions where the reaction does not proceed efficiently, raising a problem of lowered reactivity. In such a situation, if the contact time during which the reaction mixture is in contact with the immobilized enzyme is simply prolonged so as to enhance reactivity, another problem of lowered productivity (flow volume) is likely to result.

Accordingly, the present invention is to provide an efficient method for producing a useful substance, comprising carrying out a reaction by causing a liquid mixture exhibiting two liquid phases to pass through a fixed-bed reactor packed with an immobilized enzyme, wherein productivity is improved by elevating reactivity without reducing the flow volume.

The present inventors have analyzed the flow of a reaction mixture that passes through a fixed-bed reactor packed with an immobilized enzyme, and have found that when a flow channel has a smaller cross section, the reaction mixture flows in a more uniform state, to thereby improve reactivity. Based on this finding, the inventors have found that if an insertion unit or tubes are provided in the interior of a fixed-bed reactor having a large cross section packed with an immobilized enzyme so as to form lumens each having a relatively small cross section of circular shape or polygonal shape and enzymatic reaction is carried out in the respective lumens having a small cross section, enhanced productivity can be obtained while maintaining high reactivity.

According to the present invention, in a reaction performed by supplying a liquid mixture exhibiting two liquid phases to a fixed-bed reactor packed with an immobilized enzyme, flow of the entire reaction mixture in the reactor can be made uniform, to thereby improve both reactivity and productivity. In particular, in the hydrolysis of oils and fats, enzymatic activity can be effectively utilized, whereby fatty acids can be produced efficiently.

In the present invention, a liquid mixture exhibiting two liquid phases is supplied to a fixed-bed reactor packed with an immobilized enzyme. As used herein, a fixed-bed reactor (hereinafter may also be referred to as an "enzyme column") is a reactor comprising a columnar or similar structure packed with an immobilized enzyme to which a reaction mixture is applied so that the reaction mixture flows through pores of a carrier employed for immobilizing the enzyme (hereinafter referred to simply as "carrier") and spaces between carriers. The term "two liquid phases" refers to a state where two different liquids which have undergone a mixing operation do not present a single phase, and the term encompasses a phase-separated state and a uniform but emulsified state.

According to a preferred mode of the present invention, an enzyme capable of degrading oils and fats is adsorbed onto a carrier to thereby prepare the immobilized enzyme of the invention, and the enzyme-adsorbed carrier is placed in a reactor. A two phase liquid mixture composed of an oil-phase substrate and a water-phase substrate is applied to the reactor to thereby perform hydrolysis of oils and fats, producing fatty acids as useful substances.

According to the present invention, the two liquid phases flow in parallel uni-directionally. In this case, the two liquid phases may be mixed to an emulsified state in advance, or they may be supplied to the reactor in a phase-separated state. Alternatively, in supply, the two-liquid phases may take turns at predetermined times. Supply of the respective substrates to the enzyme column may be carried out downward from the top to the bottom of the reactor, or vice versa; i.e., upward.

An immobilized enzyme employed in the present invention is prepared by binding enzyme onto a carrier through adsorption, etc. Examples of the carrier include inorganic carriers such as celite, diatomaceous earth, kaolinite, silica gel, molecular sieves, porous glass, activated charcoal, calcium carbonate, and ceramics; and organic polymers such as ceramic powders, polyvinyl alcohols, polypropylene, chitosan, ion exchange resins, hydrophobic adsorption resins, chelate resins, and synthetic adsorption resins. Of these, the ion exchange resins are particularly preferred, since they have high water retention capability. Among the ion exchange resins, porous ion exchange resins are preferred, since they have a large surface area and increase the adsorption amount of an enzyme.

The particle size of the resin employed as a carrier is preferably 100 to 1000 μm, more preferably 250 to 750 μm. The pore size of the resin is preferably 10 to 150 nm, more preferably 10 to 100 nm. As the material of the resin, phenol-formaldehyde, polystyrene, acrylamide and divinylbenzene, may be employed. Of these, a phenol-formaldehyde resin (e.g., "Duolite A-568," product of Rohm and Hass) is particularly preferred, since it can attain improved enzyme adsorption.

No particular limitation is imposed on the enzyme of the immobilized enzyme of the present invention. Preferably, lipase employed for decomposing oils and fats is employed, from the viewpoint of enhancing higher productivity. The lipase to be employed may be derived from animals or plants, and also may be a commercially available lipase derived from microorganisms. Examples of the lipase derived from microorganisms include those derived from the genus *Rizopus*, genus *Aspergillus*, genus *Mucor*, genus *Pseudomonas*, genus *Geotrichum*, genus *Penicillium*, and genus *Candida*, and other microorganisms.

The temperature at which enzyme immobilization is carried out may be determined on the basis of the properties of the enzyme. Preferably, the enzyme immobilization is performed at a temperature where the enzyme is not deactivated; i.e., at 0 to 60° C., preferably at 5 to 40° C. The pH of an enzyme solution to be employed for enzyme immobilization may fall within a range not causing denaturation of the enzyme, and, similar to the determination of the immobilizing temperature, can be determined on the basis of the properties of the enzyme. Preferably, the pH range is from 3 to 9. Buffers are employed for maintaining the pH of the enzyme solution within the above range, and those include acetate buffers, phosphate buffers, and tris-HCl buffers. The enzyme concentration of the enzyme solution is preferably not greater than the saturated solubility of the enzyme, but sufficiently high for attaining improved immobilization efficiency. The enzyme solution may also be a supernatant obtained by removing insoluble matter through centrifugal separation, or a solution purified by ultrafiltration in accordance with needs. The amount of the enzyme to be employed depends on the enzymatic activity, and is preferably 5 to 1,000 weight %, more preferably 10 to 500 weight %, on the basis of the amount of the carrier.

When enzyme immobilization is performed, an enzyme may be adsorbed onto a carrier without any treatment. Preferably, before enzyme adsorption, the carrier is treated with fat-soluble fatty acids or derivatives thereof so as to obtain an adsorption state capable of exhibiting higher enzymatic activity. When the carrier is brought into contact with fat-soluble fatty acids or derivatives thereof, they may be added as such to water or an organic solvent. Alternatively, to improve dispersibility, the fat-soluble fatty acids or derivatives thereof are dispersed and dissolved in an organic solvent in advance, and the mixture may be added to the carrier dispersed in water. Examples of the organic solvent includes chloroform, hexane, and ethanol. The amount of the fat-soluble fatty acids or derivatives thereof to be employed is preferably 1 to 500 weight %, more preferably, 10 to 200 weight %, on the basis of the amount of the carrier. The contact temperature is preferably 0 to 100° C., more preferably 20 to 60° C. The contact time is preferably about 5 minutes to about 5 hours. After such treatment, the carrier is collected through filtration. Furthermore, the collected carrier may be dried. The drying temperature is preferably room temperature to 100° C., and drying may be performed under reduced pressure.

Examples of the fat-soluble fatty acids employed for pretreating the carrier include C4 to C24, preferably C8 to C18, saturated or unsaturated fatty acids (linear or branched). These fatty acids may have hydroxyl groups. Specific examples include capric acid, lauric acid, myristic acid, oleic acid, linoleic acid, α-linoleic acid, ricinoleic acid, and isostearic acid. The derivatives of the fat-soluble fatty acids include esters produced from these fat-soluble fatty acids, and monohydric alcohols, polyhydric alcohols, or sugars; phospholipids; and compounds obtained by adding ethylene oxide to these esters. Specific examples include methyl esters, ethyl esters, monoglycerides, diglycerides, compounds produced by adding ethylene oxide to these esters, polyglycerin esters, sorbitan esters, and sucrose esters. The fat-soluble fatty acids or derivatives thereof are preferably in the form of a liquid at ambient temperature, since an enzyme can be immobilized onto a carrier effectively. The fat-soluble fatty acids or derivatives thereof as described above may be employed in combination of two or more species. In addition to the above fat-soluble fatty acids or derivatives thereof, naturally-occurring fatty acids; for example, fatty acids derived from rape and soybean, may be employed.

The hydrolytic activity of the immobilized enzyme is preferably 20 U/g or higher, more preferably 100 to 10,000 U/g, even more preferably 500 to 5,000 U/g. Here, 1 U of the enzyme indicates the hydrolyzing ability of the enzyme to form 1 μmol of free fatty acids in a minute when a 100:25 (by weight) liquid mixture of oils and fats and water is hydrolyzed at 40° C. for 30 minutes while stirring and mixing the liquid mixture.

The hydrolytic activity of the immobilized enzyme per unit gram of oils and fats [U/g-oil] is substantially in inverse proportion to the time required until a certain hydrolysis ratio is reached. When hydrolysis is conducted using a packed layer (enzyme column) of an immobilized enzyme, the hydrolysis ratio differs depending on the feeding conditions (e.g., liquid flow rate and temperature). Nonetheless, the apparent activity (activity to be exhibited) [U/g] of the immobilized enzyme can be determined from the time required for the hydrolysis (the residence time in the packed layer), the weight [g-oil] of oils and fats present in the packed layer, and the packed weight [g] of the immobilized enzyme.

The oil-phase substrate employed in the present invention is mainly oils and fats. Examples of the oils and fats include not only triacylglycerol but also diacylglycerol, monoacylglycerol, fatty acid species, and fatty acids resulting from hydrolysis. Examples of the oil-phase substrate include vegetable oils such as rapeseed oil, soybean oil, sunflower oil, palm oil, linseed oil; animal oils such as beef tallow, lard, and fish oil; and oils and fats of a combination of these oils. These oils and fats to be employed may be deodorized oils and fats or non-deodorized oils and fats. When deodorized oils are employed as the oils and fats, or as a portion thereof, production of trans-unsaturated fatty acids and conjugated unsaturated fatty acids can be reduced, while vegetable sterol, vegetable sterol fatty acid esters, and tocopherol, which are derived from the oils and fats serving as a starting material, advantageously remain. The oil-phase substrate may contain oil-soluble components such as fatty acids together with the above oils and fats. The term "fatty acid species" refers to a fatty acid resulting from hydrolysis, and a mixture of the fatty acid and one or more glycerides described above.

The water-phase substrate employed in the present invention is water. The substrate may contain other water-soluble components such as glycerin obtained through hydrolysis.

No particular limitation is imposed on the shape of the fixed-bed reactor (enzyme column) employed in the present invention, so long as the column endures the pressure applied by a pump employed. Preferably, the enzyme column is surrounded by a jacket so as to adjust the temperature of the reaction liquid flowing through the column to a suitable temperature for the enzyme reaction. The internal temperature of the enzyme column is preferably adjusted to 0 to 60° C., more preferably 20 to 40° C., so as to effectively make use of the activity of the immobilized enzyme. The enzyme column may have a length required for obtaining a desired hydrolysis ratio. The length preferably ranges from 0.01 to 10 m, more preferably 0.1 to 5 m, from the viewpoint of attaining improved reactivity and reducing pressure loss of the reactor.

Figure 2:
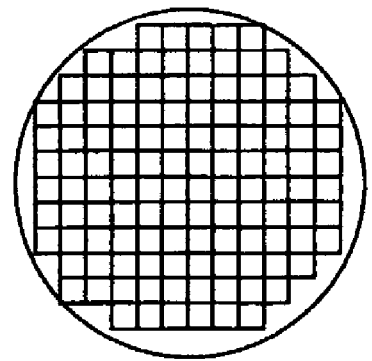
FIG. 2 shows a cross section of an enzyme column equipped with an insertion unit composed of hollow square pillar structures.
Figure 3:
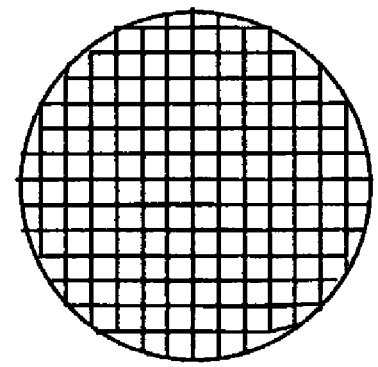
FIG. 3 shows a cross section of an enzyme column equipped with an insertion unit composed of plate-like (partition) members.

In the present invention, an insertion unit or tubes are placed in an enzyme column so as to form a plurality of lumens, each of which has a circular cross section with a diameter of 100 mm or less, or a polygonal cross section with a diagonal line length of 100 mm or less; the lumens are packed with an immobilized enzyme; and the above-mentioned liquid mixture is fed therethrough to carry out the reaction. Since each lumen has such a small cross sectional area, the cross sectional area of one flow channel becomes small. Therefore, the two-phase reaction liquid can flow through the flow channel uniformly. In this connection, if there is a space between the inner wall of the enzyme column and the insertion unit or tubes having lumens, from the viewpoint of attaining a uniform flow of reaction liquid, the space is preferably filled with an immobilized enzyme. No particular limitation is imposed on the insertion unit or tubes, so long as they can form, in the enzyme column, a structure having a plurality of lumens each having a cross sectional area as described above. Examples of the insertion unit include hollow columnar structures (FIG. 1), hollow square pillar structures (FIG. 2), and plate-like (partition) members (FIG. 3). Specifically, the structure having a plurality of lumens is formed, for example, as follows: tubes are placed in an enzyme column to thereby form a multi-tube structure; partitions (e.g., flat plates and corrugated plates) are placed in an enzyme column in a longitudinal direction; or an insertion unit composed of members each having a circular or square cross section is placed. In the case where an insertion unit is employed, each component member preferably has a cross section of an equilateral triangle, square, or equilateral hexagon, in view of an increase in placement efficiency of the insertion unit. For example, the insertion unit may be a bundle of square pipes.

The diameter or diagonal line length of each of the lumens (each of the flow channels) of the structure, formed by tubes or an insertion unit, needs to be 100 mm or less, and from the viewpoint of enhancing reactivity, preferably 75 mm or less, more preferably 50 mm or less, even more preferably 35 mm or less.

Figure 4:
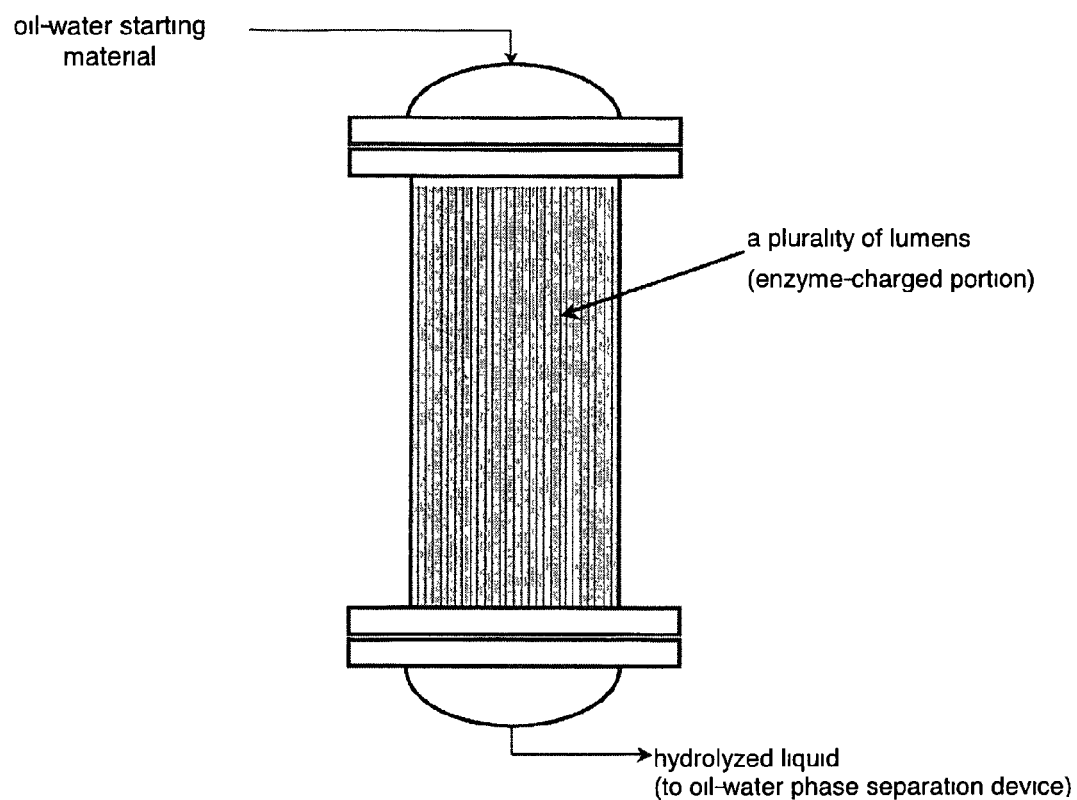
FIG. 4 shows a schematic view showing the flow of a reaction mixture through an enzyme column.

The immobilized enzyme is charged into the lumens, which are formed by placing an insertion unit or tubes in the enzyme column, and a two-phase liquid mixture (reaction mixture) is fed into the lumens (see FIG. 4).

Thus, a two-phase liquid mixture (reaction mixture) can flow through the enzyme column uniformly.

When an immobilized enzyme is charged in a reactor, if there is a space between the inner wall of the enzyme column and the insertion unit (or tubes), and if the space is excessively narrow, placement of the immobilized enzyme becomes difficult. If the space is insufficiently filled, the enzyme column as a whole is filled less uniformly. In this case, the bulk density may decrease. Further, the reaction liquid will flow less uniformly, which may drop the reaction efficiency. Therefore, the space between the inner wall of the enzyme column and the insertion unit (or tubes) preferably maintains a predetermined distance or a larger distance. Although depending on the type and particle size of the filler, and on the dimension of the insertion unit or tubes, in order to secure uniform packing of the immobilized enzyme, preferably, the narrowest portion of the space between the inner wall of the enzyme column and the insertion unit (or tubes) is 1 mm or more, more preferably 5 mm or more. In order to realize a uniform flow of reaction liquid, the upper limit of the space is preferably not more than the diameter or the length of the diagonal line of the cross section of each lumen of the insertion unit or tubes, more preferably 70 mm or less, even more preferably 50 mm or less.

The length of the insertion unit or each tube in the enzyme column is preferably not less than the height of the charged immobilized enzyme, so that all the reaction liquid can flow through the column uniformly. Furthermore, when the length is not less than 50% of the height, or 75% of the height; i.e., within a certain range in which the length is less than the height, the same effect as above can be obtained.

The insertion unit or the tube may be an integral one, having no connection part over the entire length. Preferably, an insertion unit or tubes are divided in a longitudinal direction so as to form a multi-stage structure, in view of improved operability; e.g., easy replacement of the charged immobilized enzyme. The number of stages depends on the total length of the enzyme column, and is preferably 2 to 30, more preferably 2 to 10. Each stage of the insertion unit or the tubes may be divided in a lateral direction into several parts, in view of, for example, easy loading of the insertion units or the tubes.

The linear flow rate of the reaction liquid preferably ranges 1 to 400 mm/min, more preferably 5 to 200 mm/min. The term "linear flow rate (mm/min)" as used herein means a value expressed by the quotient obtained by dividing the amount of the reaction liquid fed per minute ($mm^3$/min) (or feed speed ($10^{-3}$ mL/min)) by the cross-sectional area of the packed layer ($mm^2$). As the inner pressure of the packed column increases as a result of an increase in the linear flow rate, passing a liquid becomes difficult, and the packed column is required to be highly resistant to pressure. In addition, the immobilized enzyme may be broken due to the increased inner pressure of the column. Therefore, the linear flow rate is preferably adjusted to 400 mm/min or lower, and, from the viewpoint of enhancing productivity, is adjusted to 1 mm/min or higher. The exhibited activity of the immobilized enzyme varies depending on the linear flow rate. Therefore, when an optimal linear flow rate is determined, and reaction conditions including the rate are applied, the immobilized enzyme can be caused to react in a manner commensurate with the intended productivity and production cost.

From the viewpoint of avoiding the equilibrium of the hydrolytic reaction, obtaining activity of the immobilized enzyme more effectively, and enhancing productivity, the residence time of the liquid reaction mixture in the enzyme column preferably ranges from 30 seconds to 60 minutes, more preferably from 1 to 40 minutes. The term "residence time (min)" as used herein means a value obtained by multiplying the thickness (mm) of the packed layer by % pore, and dividing the resultant value by the linear flow rate (mm/min).

In the present invention, the reaction liquid which has flowed through an enzyme column may be employed as a final product, in consideration of reactivity, productivity, and other factors. Alternatively, the obtained reaction liquid may be partitioned between an oil-phase product and a water-phase product, and fresh water is added subsequently to the thus-obtained oil-phase product. Subsequently, the mixture may be fed into and flowed through the same enzyme column again in a manner similar to that described above. The procedure may be repeated until the desired reaction ratio is attained. Alternatively, the obtained reaction liquid may be partitioned between an oil-phase product and a water-phase product, and fresh water is subsequently added to the thus-obtained oil-phase product. Subsequently, the mixture may be fed into and flowed through another enzyme column again in a manner similar to that described above, to thereby perform the reaction in a continuous manner. The procedure may be repeated until the desired reaction ratio is attained. Alternatively, a plurality of enzyme columns is employed, and the reaction liquid obtained from each column is partitioned between the oil-phase product and water-phase product. Subsequently, the obtained oil-phase product and the obtained water-phase product are fed into the next enzyme column and the former enzyme column, respectively. Thus, the oil phase product, having a higher hydrolysis ratio, may be allowed to react with the fresh water-phase product (i.e., quasi-counterflow method). No particular limitation is imposed on the oil-water phase separation method; devices using spontaneous sedimentation, centrifugal separation, etc., are generally employed.

The following examples further describe and demonstrate embodiments of the present invention. The examples are given solely for the purpose of illustration and are not to be construed as limitations of the present invention.

EXAMPLES

Preparation of Immobilized Lipase

One part by weight of "Duolite A-568" (product of Diamond Shamrock Corporation; particle size distribution: 100 to 1,000 µm) was stirred for 1 hour in 10 parts by weight of 1/10N NaOH solution. After filtration, the carrier was washed with 10 parts by weight of deionized water, and the thus-washed carrier's pH was equilibrated with 10 parts by weight of 500 mM sulfate buffer (pH 7). Subsequently, the carrier's pH was equilibrated with 10 parts by weight of 50 mM acetate buffer (pH 7) twice, each for 2 hours. Thereafter, filtration was performed so as to collect the carrier, and the carrier was subjected to ethanol replacement with 5 parts by weight of ethanol for 30 minutes. After filtration, 5 parts by weight of ethanol containing 1 part by weight of ricinolic acid were added, and the carrier was allowed to adsorb the ricinolic acid thereon for 30 minutes. Filtration was performed to collect the carrier, followed by washing with 5 parts by weight of 50 mM acetate buffer (pH 7) four times, each for 30 minutes, so as to remove ethanol. Filtration was then performed to collect the carrier. Subsequently, the carrier was kept in contact with an enzyme solution, which had been prepared by dissolving 1 part by weight of commercially available lipase ("Lipase AY Amano", product of Amano Enzyme Inc.) in 9 parts by weight of 50 mM acetate buffer (pH 7), for 5 hours to perform enzyme immobilization. The immobilized enzyme was collected by filtration, and washed with 10 parts by weight of 50 mM acetate buffer (pH 7) so as to remove unimmobilized enzyme and proteins. Thereafter, 4 parts by weight of soybean oil to be actually subjected to hydrolysis were added, and the thus-obtained mixture was stirred for 12 hours. The above procedure was performed entirely at 20° C. Filtration was then performed to separate the immobilized enzyme from the oil. The thus-obtained immobilized lipase had 2,700 U/g (dry weight) of hydrolytic activity (exhibitable activity). The weight-basis average particle size of the immobilized enzyme was found to be 451 µm.

Example 1

An insertion unit was produced by bundling 40 square pipes. Each pipe has a square cross section of 24 mm×24 mm (wall thickness: 1.5 mm, height: 300 mm). Five insertion units were stacked in a stainless column (inner diameter: 200 mm, height: 1,600 mm) equipped with a jacket (total height of the units: 1,500 mm). The above-prepared immobilized lipase (10.5 kg (dry weight)) was charged into the column (charged height of the immobilized lipase: 1,500 mm), and the temperature of the column was maintained at 35° C. by use of the jacket. A mixture of rapeseed oil and distilled water (10:6 by weight) was fed into the top of the column at 30 kg/Hr, to thereby perform hydrolysis. Table 1 shows the results. Each hydrolysis ratio shown in Table 1 was determined by dividing an acid value obtained through analysis by a saponification value. Notably, the acid value was determined through the method described in "American Oil Chemists. Society Official Method Ca 5a-40," and the saponification value was determined through the method described in "American Oil Chemists. Society Official Method Cd 3a-94".

Example 2

An insertion unit was produced by bundling 16 square pipes. Each pipe has a square cross section of 35 mm×35 mm (wall thickness: 1.5 mm, height: 300 mm). Five insertion units were stacked in a stainless column (inner diameter: 200 mm, height: 1,600 mm) equipped with a jacket (total height of the units: 1,500 mm). The above-prepared immobilized lipase (11.4 kg (dry weight)) was charged into the column (charged height of the immobilized lipase: 1,500 mm). Other procedures were performed for hydrolysis in a manner similar to that employed in Example 1. Table 1 shows the results.

Example 3

An insertion unit was produced by bundling 7 square pipes. Each pipe has a square cross section of 52 mm×52 mm (wall thickness. 1.5 mm, height: 300 mm). Five insertion units were stacked in a stainless column (inner diameter: 200 mm, height: 1,600 mm) equipped with a jacket (total height of the units: 1,500 mm). The above-prepared immobilized lipase (11.9 kg (dry weight)) was charged into the column (charged height of the immobilized lipase: 1,500 mm). Other procedures were performed for hydrolysis in a manner similar to that employed in Example 1. Table 1 shows the results.

Example 4

An insertion unit was produced by bundling 4 square pipes. Each pipe has a square cross section of 70 mm×70 mm (wall thickness: 1.5 mm, height: 300 mm). Five insertion units were stacked in a stainless column (inner diameter: 200 mm, height: 1,600 mm) equipped with a jacket (total height of the units: 1,500 mm). The above-prepared immobilized lipase (12.1 kg (dry weight)) was charged into the column (charged height of the immobilized lipase: 1,500 mm). Other procedures were performed for hydrolysis in a manner similar to that employed in Example 1. Table 1 shows the results.

Example 5

An insertion unit was produced by bundling 16 square pipes. Each pipe has a square cross section of 37 mm×37 mm (wall thickness: 1.5 mm, height: 300 mm). Five insertion units were stacked in a stainless column (inner diameter: 200 mm, height: 1,600 mm) equipped with a jacket (total height of the units: 1,500 mm). The above-prepared immobilized lipase (10.7 kg (dry weight)) was charged into the column (charged height of the immobilized lipase: 1,500 mm). Other procedures were performed for hydrolysis in a manner similar to that employed in Example 1. The distance between the insertion unit and the inner, wall of the column, as measured at the narrowest portion, was found to be 0.35 mm. Table 1 shows the results.

Comparative Example 1

The procedure of Example 1 was repeated for performing hydrolysis, except that no square pipes were placed in a stainless column, and the above prepared immobilized lipase (12.7 kg (dry weight)) was charged into the column (height of the charged immobilized lipase: 1,500 mm). Table 1 shows the results.

TABLE 1

|  | Ex. 1 | Ex. 2 | Ex. 3 | Ex. 4 | Ex. 5 | Comp. Ex. 1 |
|---|---|---|---|---|---|---|
| Cross section of insertion component (mm) | 24 × 24 | 35 × 35 | 52 × 52 | 70 × 70 | 37 × 37 | — |
| Number of components | 40 | 16 | 7 | 4 | 16 | — |
| Minimum distance between the insertion unit and the inner wall of the reactor (mm) | 3 | 6 | 6 | 1 | 0.35 | — |
| Amount of charged enzyme (kg) | 10.5 | 11.4 | 11.9 | 12.1 | 10.7 | 12.7 |
| Pore volume of charged enzyme | 0.56 | 0.56 | 0.56 | 0.56 | 0.58 | 0.56 |
| Hydrolysis ratio (%) | 90 | 90 | 85 | 82 | 80 | 77 |
| Apparent activity of immobilized enzyme (U/g) | 950 | 926 | 616 | 475 | 420 | 354 |

As is clear from Table 1, when rapeseed oil and distilled water were fed into the fixed-bed reactor having a plurality of lumens, each having a certain cross sectional area, formed by the use of an insertion unit, the hydrolysis ratio is improved, and the (apparent) activity of the immobilized enzyme is exhibited effectively. When there is a narrow space between the inner wall of the fixed-bed type reactor and the insertion unit, void fraction as measured after packing of the immobilized enzyme is somewhat high, with a tendency of a low hydrolysis ratio. But these tendencies were found to be eliminated by making the distance of the narrow space 1 mm or more.

The invention claimed is:

1. A method for producing a fatty acid, the method comprising: supplying, to a fixed-bed reactor packed with an immobilized lipase, a liquid mixture comprising two liquid phases formed of an oil-phase substance comprising oils and fats and a water-phase substance, wherein the two liquid phases flow in an identical, parallel direction, wherein the fixed-bed reactor is equipped with an insertion unit or tubes, so as to form a plurality of lumens in the fixed-bed reactor, wherein each lumen has a cross section of a circular shape with a diameter of 75 mm or less or has a polygonal shape with a diagonal line of 75 mm or less, wherein the lumens are packed with the immobilized lipase and the liquid mixture is supplied through the packed immobilized lipase.

2. The method according to claim 1, wherein one component of the liquid mixture is a vegetable oil, an animal oil, or mixture thereof.

3. The method according to claim 1, wherein the insertion unit or tubes are vertically divided into a plurality of subunits.

4. The method according to claim 1, wherein the insertion unit or tubes are laterally divided into a plurality of subunits.

5. The method according to claim 1, wherein the narrowest portion of a space between the inner wall of the fixed-bed reactor, which is an enzyme column, and the insertion unit or tubes is 1 mm or more.

6. The method according to claim 1, wherein the lipase is immobilized on a carrier selected from the group consisting of an inorganic carrier and an organic carrier.

7. The method according to claim 6, wherein the lipase is immobilized on the inorganic carrier is selected from the group consisting of celite, diatomaceous earth, kaolinite, silica gel, molecular sieves, porous glass, activated charcoal, calcium carbonate, ceramics, and a mixture thereof.

8. The method according to claim 6, wherein the lipase is immobilized on the organic carrier is selected from the group consisting of a ceramic powder, a polyvinyl alcohol, polypropylene, chitosan, an ion exchange resin, a hydrophobic adsorption resin, a chelate resin, a synthetic adsorption resin, and a mixture thereof.

9. The method according to claim 8, wherein a particle size of the organic carrier is from 100 to 1,000 µm.

10. The method according to claim 1, wherein the hydrolytic activity of the lipase is 20 U/g or greater.

11. The method according to claim 5, wherein the enzyme column is surrounded by a jacket.

12. The method according to claim 5, wherein the internal temperature of the enzyme column is adjusted to 0 to 60° C.

13. The method according to claim 5, wherein the internal temperature of the enzyme column is adjusted to 20 to 40° C.

14. The method according to claim 1, wherein the insertion unit or tubes are divided in a longitudinal direction so as to form a multi-stage structure, wherein the number of stages is from 2 to 30.

15. The method according to claim 1, wherein the linear flow rate of the liquid mixture is from 1 to 400 mm/min.

16. The method according to claim 1, wherein each lumen has a cross section of a circular shape with the diameter of 50 mm or less or has a polygonal shape with a diagonal line of 50 mm or less.

17. The method according to claim 1, wherein each lumen has a cross section of a circular shape with the diameter of 35 mm or less or has a polygonal shape with a diagonal line of 35 mm or less.

18. The method according to claim 1, wherein the two-phase liquid mixture is supplied to the plurality of lumens simultaneously and flows through the enzyme column uniformly.

19. The method according to claim 1, wherein the two-phase liquid mixture is supplied to the plurality of lumens in each stage of the a multi-stage structure simultaneously and flows through the enzyme column uniformly.

20. The method according to claim 1, wherein the height of each of the lumens is greater than the diameter or the diagonal line.

21. The method according to claim 1, wherein the diameter or the diagonal line of each of the lumens is smaller than a diameter of the enzyme column.

* * * * *